(12) United States Patent
Brown et al.

(10) Patent No.: US 7,000,457 B2
(45) Date of Patent: Feb. 21, 2006

(54) METHODS TO CONTROL AND/OR PREDICT RHEOLOGICAL PROPERTIES

(75) Inventors: Steven E. Brown, Tyngsboro, MA (US); Ian D. Morrison, Acton, MA (US)

(73) Assignee: Cabot Corporation, Boston, MA (US)

(*) Notice: Subject to any disclaimer, the term of this patent is extended or adjusted under 35 U.S.C. 154(b) by 0 days.

(21) Appl. No.: 10/649,348

(22) Filed: Aug. 27, 2003

(65) Prior Publication Data

US 2004/0194537 A1    Oct. 7, 2004

Related U.S. Application Data

(60) Provisional application No. 60/459,230, filed on Apr. 1, 2003, provisional application No. 60/485,964, filed on Jul. 10, 2003, provisional application No. 60/485,965, filed on Jul. 10, 2003, provisional application No. 60/491,632, filed on Jul. 31, 2003.

(51) Int. Cl.
*G01N 15/06* (2006.01)
*G01N 11/00* (2006.01)

(52) U.S. Cl. ........................... 73/61.71; 73/53.01
(58) Field of Classification Search .............. 73/54.01, 73/54.22
See application file for complete search history.

(56) References Cited

U.S. PATENT DOCUMENTS

| | | | |
|---|---|---|---|
| 3,229,507 A | 1/1966 | Sljaka et al. | 73/59 |
| 3,627,677 A * | 12/1971 | Dyrud | 210/649 |
| 3,659,896 A | 5/1972 | Smith et al. | 296/93 |
| 3,764,527 A * | 10/1973 | Sohl | 210/671 |
| 4,071,496 A | 1/1978 | Kraus et al. | 260/42.36 |
| 4,088,628 A | 5/1978 | Bernstein et al. | 260/42.46 |
| 4,093,421 A | 6/1978 | Jerkins | 23/259.5 |
| 4,167,110 A * | 9/1979 | Kopito et al. | 73/54.22 |
| 4,237,725 A * | 12/1980 | Kopito et al. | 73/54.22 |
| 4,255,296 A | 3/1981 | Ogawa et al. | 260/5 |
| 4,259,218 A | 3/1981 | Haws | 260/5 |
| 4,360,627 A | 11/1982 | Okado et al. | 524/496 |
| 4,478,973 A | 10/1984 | Misono et al. | 524/496 |
| 4,540,560 A | 9/1985 | Henderson et al. | 423/445 |
| 4,548,980 A | 10/1985 | Nagata et al. | 524/495 |
| 4,678,830 A | 7/1987 | Sato et al. | 524/495 |
| 4,690,965 A | 9/1987 | Hirata et al. | 524/236 |

(Continued)

FOREIGN PATENT DOCUMENTS

EP    0253290    1/1988

(Continued)

OTHER PUBLICATIONS

M. Holz, "Rheological Phenomina and Structure Formation in Multiphase Polymers," Feb. 2001, internet publication, pp. 1-5.*

(Continued)

*Primary Examiner*—Hezron Williams
*Assistant Examiner*—John Fitzgerald (57) ABSTRACT

Methods to predict the rheological properties of composition comprising a filler in a matrix are described. The present invention further involves determining the difference between the work of cohesion and the work of ahhesion for a filler and a matrix in order to quantitatively predict the rheological properties of the system, such as yield point. The ability to predict such properties has numerous advantages. The present invention further relates to a rheological master curve and a method to produce the curve which permits one to predict a rheological property of a composition comprising a filler in a matrix based on the particular polymer used and the particular filler used. Also disclosed is a method of method of choosing a filler to achieve a desired rheological property using the rheological master curve described herein.

11 Claims, 4 Drawing Sheets

Yield Stress versus Delta Work

U.S. PATENT DOCUMENTS

| | | | |
|---|---|---|---|
| 4,721,740 A | 1/1988 | Takeshita et al. | 523/215 |
| 4,878,379 A | 11/1989 | Deer | 73/60 |
| 4,914,147 A | 4/1990 | Mouri et al. | 524/495 |
| 4,992,190 A | 2/1991 | Shtarkman | 252/62.52 |
| 5,093,407 A | 3/1992 | Komai et al. | 524/495 |
| 5,124,396 A | 6/1992 | Branon, Jr. et al. | 524/496 |
| 5,128,395 A | 7/1992 | Terakawa et al. | 524/274 |
| 5,162,421 A | 11/1992 | Ue et al. | 524/495 |
| 5,190,739 A | 3/1993 | MacKay et al. | 423/450 |
| 5,194,488 A | 3/1993 | Piestert et al. | 524/703 |
| 5,211,932 A | 5/1993 | Blaylock et al. | 423/450 |
| 5,231,129 A | 7/1993 | Misono | 524/496 |
| 5,232,974 A | 8/1993 | Branan, Jr. et al. | 524/495 |
| 5,288,788 A | 2/1994 | Shieh et al. | 524/495 |
| 5,292,790 A | 3/1994 | Shimizu et al. | 524/496 |
| 5,303,578 A | 4/1994 | Williams et al. | 73/54.24 |
| 5,310,777 A | 5/1994 | Sekido et al. | 524/496 |
| 5,321,072 A | 6/1994 | Misono | 524/496 |
| 5,322,724 A | 6/1994 | Levens | 428/57 |
| 5,322,874 A | 6/1994 | Fujii et al. | 524/227 |
| 5,352,289 A | 10/1994 | Weaver et al. | 106/476 |
| 5,362,794 A | 11/1994 | Inui et al. | 624/496 |
| 5,382,621 A | 1/1995 | Laube | 524/496 |
| 5,405,623 A | 4/1995 | Barkalow et al. | 426/5 |
| 5,426,148 A | 6/1995 | Tucker | 524/496 |
| 5,428,099 A | 6/1995 | Morrar et al. | 524/495 |
| 5,430,087 A | 7/1995 | Carlson et al. | 524/496 |
| 5,480,626 A | 1/1996 | Klasen et al. | 423/449.1 |
| 5,534,578 A | 7/1996 | Wideman et al. | 524/396 |
| 5,547,609 A | 8/1996 | Fujii et al. | 252/511 |
| 5,639,817 A | 6/1997 | Probst et al. | 524/496 |
| 5,643,991 A | 7/1997 | Stipe et al. | 524/496 |
| 5,652,298 A | 7/1997 | Murray | 524/571 |
| 5,688,317 A | 11/1997 | MacKay et al. | 106/476 |
| 5,696,197 A | 12/1997 | Smith et al. | 524/495 |
| 5,705,555 A | 1/1998 | Guilfoy et al. | 524/495 |
| 5,714,096 A | 2/1998 | Dorfman | 252/511 |
| 5,723,531 A | 3/1998 | Visel et al. | 524/496 |
| 5,731,229 A * | 3/1998 | Kato et al. | 438/50 |
| 5,733,480 A | 3/1998 | Lee et al. | 252/511 |
| 5,792,941 A | 8/1998 | Rye et al. | 73/53.01 |
| 5,801,209 A | 9/1998 | Chung et al. | 521/99 |
| 5,859,120 A | 1/1999 | Karl et al. | 524/495 |
| 5,877,250 A | 3/1999 | Sant | 524/496 |
| 5,877,251 A | 3/1999 | Sant | 524/496 |
| 5,974,167 A | 10/1999 | Reszler | 382/141 |
| 6,013,737 A | 1/2000 | Takagishi et al. | 525/332.7 |
| 6,046,266 A | 4/2000 | Sandstrom et al. | 524/492 |
| 6,056,933 A | 5/2000 | Vogler et al. | 423/449.1 |
| 6,084,015 A | 7/2000 | Chino et al. | 524/189 |
| 6,086,792 A | 7/2000 | Reid et al. | 252/511 |
| 6,096,833 A | 8/2000 | Araki et al. | 525/342 |
| 6,099,818 A | 8/2000 | Freund et al. | 423/449.1 |
| 6,156,837 A | 12/2000 | Branan, Jr. et al. | 524/495 |
| 6,224,713 B1 * | 5/2001 | Hembree et al. | 156/345.13 |
| 6,228,928 B1 | 5/2001 | Soeda et al. | 524/495 |
| 6,277,350 B1 | 8/2001 | Gerspacher | 423/449.1 |
| 6,391,274 B1 | 5/2002 | Vogler et al. | 423/275 |
| 6,410,630 B1 | 6/2002 | Hoover et al. | 524/365 |
| 6,448,309 B1 | 9/2002 | Mahmud et al. | 523/215 |
| 6,652,918 B1 * | 11/2003 | Lee et al. | 427/387 |
| 6,690,179 B1 * | 2/2004 | Hajduk et al. | 324/663 |
| 2001/0036995 A1 | 11/2001 | Mahmud et al. | 524/495 |
| 2002/0077409 A1 | 6/2002 | Sakaki et al. | 524/496 |
| 2002/0107318 A1 * | 8/2002 | Yamada et al. | 524/495 |
| 2002/0156177 A1 | 10/2002 | Freund | 524/496 |
| 2002/0173582 A1 | 11/2002 | Schmidt | 524/504 |
| 2003/0097871 A1 | 5/2003 | Mansky | 73/64.49 |
| 2003/0162876 A1 | 8/2003 | Vanier et al. | 524/437 |
| 2003/0164027 A1 | 9/2003 | Terrom | 73/64.48 |

FOREIGN PATENT DOCUMENTS

| | | |
|---|---|---|
| EP | 0453625 | 10/1991 |
| EP | 0919801 | 6/1999 |
| GB | 2378716 | 2/2003 |

OTHER PUBLICATIONS

A.M. Voelkel, "Preliminary Program: Second International Symposium on Acid-Base Interactions: Relevance to Adhesion," Jul. 1998, internet publication, pp. 1-19.*

The Society of Rheology, Journal of Rheology, vol. 41, issue 2, Apr. 1997, vol. 42, issue 3, May 2001, vol. 45, issue 4, Aug. 2001.*

"Bound Rubber and Carbon Black Reinforcement," by E. M Dannenberg, 1986, pp. 512-524.

"Filler-Elastomer Interactions. Part VII. Study on Bound Rubber," by Siegfried Wolff et al., reprinted from Rubber Chemistry and Technology, vol. 66, No. 2, May-Jun. 1993, 163-177.

"Standard Test Method for Carbon Black—Iodine Adsorption Number," ASTM Designation D 1510-99, pp. 271-275.

"Standard Test Method for Carbon Black—CTAB (Cetyltrimethylammonium Bromide) Surface Area," ATSM Designation D 3765-99, pp. 563-568.

"Standard Test Methods for Carbon Black—Surface Area by Multipoint B.E.T. Nitrogen Adsorption," ATSM Designation D 4820-97, pp. 763-769.

"Standard Test Methods for Carbon Black—External Surface Area by Multipoint Nitrogen Adsorption," ATSM Designation D 5816-96, pp. 878-880.

"Standard Test Method for Carbon Black—Total and External Surface Area by Nitrogen Adsorption," ATSM Designation D 6556-00a, pp. 970-974.

"Roles of Work of Adhesion between Carbon Blacks and Thermoplastic Polymers on Electrical Properties of Composites," by Soo-Jin Park et al., published in the Journal of Colloid and Interface Science 255, pp. 145-149 (2002).

"Component Interactions and the Stability of Some Pigment/Polymer Dispersions," by P. Mukhopadhyay et al., published in the Journal of Applied Polymer Science, vol. 67, pp. 245-253 (1998).

"Adhesion and Components of Solid Surface Energies," by John H. Clint, published in Current Opinion in Colloid & Interface Science 6, pp. 28-33 (2001).

"Estimation of the Reliability of Hansen-Parameters of Photooxidative Degraded Polymer Films by Contact Angle Measurements," by Anita Horn et al., Hildesheim, Germany, pp. 1-12.

"Basic and Acidic Surface Oxides on Carbon Fiber and Their Influence on the Expected Adhesion to Polyamide," by A. Bismarck et al., published in Colloids and Surfaces, A: Physiochemical and Engineering Aspects 159, pp. 341-350 (1999).

International Search Report and Written Opinion for PCT/US2004/010261 dated Oct. 19, 2004.

International Search Report and Written Opinion for PCT/US2004/010267 dated Oct. 15, 2004.

International Search Report and Written Opinion for PCT/US2004/010259 dated Oct. 21, 2004.

Attachment A—Development History.

Strom, "Wetting studies related to offset printing," vol. 50-04C, pp. 768 (1988) Abstract only.

Tikhonov, "On the evaluation of the work of adhesion, cohesion, and surface tension of high—viscous and solid bodies," Kolloidn Zh, vol. 53, No. 3, pp. 552-558 (1991) Abstract only.

Janczuk, et al., "Surface free energy components and adsorption properties of some porous glasses," Mater Chem Phys. vol. 25, No. 2, pp. 185-198 (1990) Abstract only.

Janczuk, et al., "Surface free energy of celestite and its flotation activity," Colloids Surf. vol. 35, No. 1, pp. 41-48 (1989) Abstract only.

Wojcik et al., "Gas-adsorption studies on correlations between the flotability of minerals and the work of water adhesion to their surfaces," Colloids Surf. vol. 30, No. 3-4, pp. 275-285 (1988) Abstract only.

Lipatov, "Adhesion at the polymer mixtures-solid interface, " Vide, Couches Minces, vol. 50 (274), pp. 415-420 (1994) Abstract only.

Hill, "Wall slip in polymer melts: A pseudo-chemical model, " J. Rheol. vol. 42, No. 3, pp. 581-601 (1998) Abstract only.

Scheie, "The upward force on liquid in a capillary tube," Am. J. Phys. vol. 57, No. 3, pp. 278-289 (1989) Abstract only.

Lee et al., "Effects of polymer-filler interaction on the mechanical properties of nylon 6,6 filled with organosilane-treated fillers," J. Adhes. Sci. Technol., vol. 3, No. 4, pp. 291-303 (1989) Abstract only.

Abramzon et al., "Determination of the work of adhesion and cohesion" ZH. Prikladnoi Khim, vol. 53, No. 5, pp. 1040-1043 (1980) Abstract only.

Mangipudi et al., Direct measurement of molecular level adhesion between poly(ethylene terephthalate) and polyethylene films: Determination of surface and interfacial energies, J. Adhesion Sci. Technol., vol. 8, No. 11, pp. 1251-1270 (1994) Abstract only.

Owen, "Surface properties of silicone release coatings," Proc. First Internat. Congress on Adhesion Science and Technology, pp. 255-263 (1995) Abstract only.

Kaya, The effect of pore fluid contamination on a selected physico-chemical parameters of fine grained soils (Adsorption, Conductivity), vol. 57-05B, p. 3354 (1996) Abstract only.

Qin, Adhesion properties of polymeric materials (Asphalts, Cohesion), vol. 57-02B, p. 1260 (1995) Abstract only.

Stepanov, "Electrocapillary behaviour of liquid bismuth in binary melts of strontium chloride with sodium and cesium chlorides," Ehlektrokhimiya, vol. 30, No. 8, pp. 1032-1038 (1994) Abstract only.

Kulawik, et al., "Kinetics of the molecular interactions in some extraction system," ISEC '88 International solvent extraction Conference, vol. 2, pp. 77-78 (1988) Abstract only.

Nardin et al., "Stress transfer analysis in fibre/elastomer interfaces," Comptes-Rendus des Huitiemes Journess Nationales sur les Composites, pp. 289-300 (1992) Abstract only.

Maugis, "Adherence and Fracture Mechanics," Adhesive Bonding, pp. 303-335 (1991) Abstract only.

Wan et al., "Surface forces at crack interfaces in mica in the presence of capillary condensation," Acta Metallurgia et Materialia, vol. 38, No. 11, pp. 2073-2083 (1990) Abstract only.

Savenko et al., "Effect of diamond-like carbon coatings on the mechanical properties of subsurface layers of single crystals of silicon," Physics and Chemistry of Materials Treatment, vol. 31, No. 2, pp. 149-153 (1997) Abstract only.

Lellig et al., "Glass and polymer: wetting and adhesion," Glass Science and Technology, vol. 69, No. 11, pp. 357-367 (1996) Abstract only.

Maugis, "Adherence of elastomers: fracture mechanics aspects," Journal of Adhesion, vol. 23, No. 1, pp. 61-66 (1987) Abstract only.

Riande et al., "Fundamental aspects of the adhesion of polymers," Revista de Plasticos Modernos, vol. 80, No. 530, pp. 170-179 (2000) Abstract only.

Gilbert, "Surface treatments for particulate fillers in plastics, " Plastics Additivies. AN A-Z reference, pp. 590-603 (1998) Abstract only.

Maltese, "Interfacial energy between polymers," Materie Plastiche ed Elastomeri, VBol. 64, Nos. 1 / 2, pp. 74-78 (1999) Abstract only.

Cherry et al., "Predicting work of adhesion using molecular modeling," Adhesion '96, Conference Proced., vol. 1, pp. 299-304 (1996) Abstract only.

Feinerman et al., "Rule of interfacial equilibrium," J. Adhesion, vol. 60, Nos. 1-4, pp. 99-112, (1997) Abstract only.

Geraghty et al., "Investigation of parameters influencing bioadhesive properties of myverol 18-99/water gels," Biomaterials, vol. 18, No. 1, pp. 63-67 (1997) Abstract only.

Wimolkiatisak et al., Directly paintable, high adhesion polyolefin compounds, Plast' 21 No. 43, pp. 44-47 (1995) Abstract only.

Drzal, et al., "Adhesion of carbon fibres to polycarbonate matrices: interphase composition and structure," Antec '95. vol. II, Conference Proceedings, pp. 2877-2881 (1995) Abstract only.

Moore, "Wetting in rubber-to-metal bonding agents," Rubb. Plast. News, vol. 24, No. 7, pp. 17-18 (1994) Abstract only.

Mangipudi et al., "Adhesion of thin polymer films: Effects of surface and interfacial energies and rheological properties," Antec '93 Conference Proceedings, vol. III, pp. 3099-3100, (1993) Abstract only.

Bautista et al., "Surface characterization of polypropylene used as a matrix in composite materials," Rev. Plast. Mod. vol. 66, No. 449, pp. 505-509 (1993) Abstract only.

Pritykin et al., "New thermodynamic characteristics of polymer adhesive properties," International Adhesion Conference, p 11.1-3 (1984) Abstract only.

Moskvitin, Physiocochemical Principles of Gluing and Adhesion processes, NSF, Rpt. No. SFCSI-Agr (TT-68-50368, p. 197 (1969) Abstract only.

Mayne, "Further developments with epoxy/polyamine films, " Corros. Sci., vol. 35, Nos. 5/8, pp. 1359-1361 (1993) Abstract only.

Padday, "Spreading, wetting, and contact angles," J. Adhes. Sci. Tech., vol. 6, No. 12, pp. 1347-1358 (1992) Abstract only.

Mark, "Future improvements in cohesive strength of polymers. I.," Adhesives Age, vol. 22, No. 7, pp. 35-40 (1979) Abstract only.

Hansen, "The three dimensional solubility parameter—key to paint component affinities: I. Solvents, Plasticizers, Polymers, and Resins," Journal of Paint Technology, vol. 39, No. 505, pp. 104-117 (1967).

Hansen, "The three dimensional solubility parameter—key to paint component affinities: II and III—II. Solvents, Plasticizers, Polymers, and Resins," Journal of Paint Technology, vol. 39, No. 511, pp. 505-510 (1967).

Hansen, "III. Independent calculation of the parameter components," Journal of Paint Technology, vol. 39, No. 511, pp. 511-514 (1967).

Hansen et al., "On the use of cohesion parameters to characterize surfaces," J. Adhesion, vol. 15, pp. 275-286 (1983).

Hansen, "Cohesion parameters for surfaces, pigments, and fillers," Surface Coatings International vol. 8, pp. 386-391, (1997).

Shareef et al., "Suspension interaction of pigments in solvents: characterization of pigment surfaces in terms of three-dimensional solubility parameters of solvents," Journal of Coatings Technology, vol. 58, No. 733, pp. 35-44 (1986).

Vinther, "Application of the concepts solubility parameter and pigment charge," Chemie des Peintures Engl. vol. 34, No. 10, pp. 363-372 (1971).

Schreiber, "Solvent balance, dispersion and rheological properties of pigmented polymer compositions," Journal of Paint Technology, vol. 46, No. 598, pp. 35-39 (1974).

Burrell, "The challenge of the solubility parameter concept," Journal of Paint Technology, vol. 40, No. 520, pp. 197-208 (1968).

Trudgian, "The pattern of solvent-resin-pigment affinities," Official Digest, Presented at the 41st Annual Meeting of the Federation of Societies for Paint Technology, pp. 1210-1231 (1963).

Schroder, Colloid chemistry aids to formulating inks and paints, Harmonization of the energetics of raw materials by using the solubility parameter concept, vol. 5, No. 98, pp. 334-340 (no date).

Chasey, "Methods for evaluating oil/polymer interactions in carbon black filled compounds," Rubber World, pp. 35-40 (1993).

Wolff, et al., "Filler-elastomer interactions. Part VII. Study on bound rubber," Rubber Chemistry and Technology, vol. 66, No. 2, pp. 163-177 (1993).

Barton, "CRC Handbook of solubility parameters and other cohesion parameters," pp. 1-21, (1991).

Kaya, et al., "Interfacial parameters and work of adhesion in soil-liquid systems," Geotechnical Testing Journal, vol. 23, No. 4, pp. 464-471 (2000).

Skaarup, "The three dimensional solubility parameter and its use—II. Pigmented Systems," pp. 28-42 (no date).

Grubenmann, "The solvent dependence of the solubility of organic solids, and solubility parameter theory: investigation by means of an organic pigment," Dyes and Pigments, vol. 21, pp. 273-292 (1993).

* cited by examiner

METHODS TO CONTROL AND/OR PREDICT RHEOLOGICAL PROPERTIES

This application claims the benefit under 35 U.S.C. §119 (e) of prior U.S. Provisional Patent Application Nos. 60/459,230 filed Apr. 1, 2003, 60/485,964 filed Jul. 10, 2003, 60/485,965 filed Jul. 10, 2003, and 60/491,632 filed Jul. 31, 2003, which are all incorporated in its entirety by reference herein.

BACKGROUND OF THE INVENTION

The present invention relates to a method for predicting the rheological properties of compositions comprising a filler in a matrix. The present invention further relates to a method of choosing a filler for a composition in order to achieve a desired rheological property.

In polymer or solvent-based compositions, other components may be added which contribute to the composition's ultimate properties. For instance, with respect to a polymeric composition, such as polyurethane, a filler or other particle is often present. However, in the past, typically the choice of a filler for a composition is not as elementary as simply picking any filler and adding it to the composition. In fact, it is known in the industry that each filler performs differently with respect to, for example, rheological properties. Thus, and strictly as an example, carbon black can be used as a filler, and it has been shown that one type of carbon black having certain properties such as a particular BET surface area, a DBP, tint strength, and the like can impart desirable rheological properties to a polymer composition while another carbon black having the same or similar physical parameters will not impart the same desirable rheological properties. Due to this phenomenon, in the industry, it was quite common to use past experiences in an effort to determine what filler would best interact with the components of a composition. However, even this strategy does not often work since, for example, various polymer compositions can differ from past polymer compositions, which results in the filler not providing the same desirable rheological properties.

Thus, it was quite common in the industry to simply use a hit and miss strategy wherein a carbon black or other filler is tested in a composition and then compared with another filler that is tested in the same composition until the desired rheological properties are achieved. This hit and miss strategy is quite costly, takes large blocks of time, and further does not result in the best filler being used to provide the most optimized rheological properties in the particular composition.

Thus, there is a need in the industry to provide a means to determine the best class of fillers for a particular compositikn in order to achieve the most optimized rheological properties for the composition.

SUMMARY OF THE PRESENT INVENTION

A feature of the present invention is to provide a means to choose fillers that will provide the most optimized rheological properties in a composition.

Another feature of the present invention is to provide a method to predict the rheological properties of a composition based on the use of a particular filler.

A further feature of the present invention is to provide filler-matrix combinations which provide desirable rheological properties depending on the use of the composition.

An additional feature of the present invention is to provide a means to change the rheology of a matrix by controlling the particular filler used.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method for determining a rheological master curve for a composition comprising a filler in a matrix. The method comprises the steps of:
  a) determining the work of adhesion of the matrix to the filler;
  b) determining the work of cohesion of the filler;
  c) determining the difference between the work of cohesion and the work of adhesion;
  d) measuring a rheological property of the composition; and
  e) correlating the rheological property to the difference between the work of cohesion and the work of adhesion.

The works of adhesion and cohesion are preferably determined by measuring contact angle(s) or related properties (such as wicking rates) of a filler based on one or more probe fluids. The method can be repeated any number of times with different fillers, loading levels, and the like in order to determine the best filler for the polymer matrix.

The present invention further relates to a rheological master curve for a composition comprising a filler in a matrix, wherein the master curve correlates i) the difference between the work of cohesion of the filler and the work of adhesion of the matrix to the filler; and ii) a rheological property of the composition. This rheological master curve can be created for a variety of fillers (depending on morphology, loading levels and the like) based on the present invention.

The present invention further relates to a method of predicting a value for a rheological property of a composition comprising a filler in a matrix. The method comprises the steps of:
  a) determining the work of adhesion of the matrix to the filler;
  b) determining the work of cohesion of the filler;
  c) determining the difference between the work of cohesion and the work of adhesion; and
  d) correlating the difference between the work of cohesion and the work of adhesion to the value for the rheological property using the rheological master curve described herein.

The present invention further relates to a method of choosing a filler to achieve a desired value of a rheological property of a composition comprising the filler in a matrix. The method comprises the steps of:
  a) determining the surface energy components of several probe fillers;
  b) measuring the rheological property of a composition comprising one probe filler and the matrix;
  c) correlating the rheological property of the composition comprising the probe filler and the matrix to a difference between the work of cohesion of the probe filler and the work of adhesion of the matrix to the probe filler using the rheological master curve described herein;

d) repeating steps b) and c) for each probe filler;

e) calculating the surface energy components of the matrix from the correlated differences of step c) and the surface energy components of the probe fillers of step a);

f) correlating the desired value of the rheological property of the composition comprising the filler in the matrix to a difference between the work of cohesion of the filler and the work of adhesion of the matrix to the filler using the rheological master curve described herein;

g) choosing the target filler having the surface energy components which, when used to calculate the work of cohesion of the target filler and the work of adhesion of the matrix to the target filler, gives a difference which is similar to the correlated difference of step f).

It is to be understood that both the foregoing general description and the following detailed description are exemplary and explanatory only and are intended to provide a further explanation of the present invention, as claimed.

The accompanying drawings, which are incorporated in and constitute a part of this application, illustrate various aspects of the present invention and together with the description serve to explain the principles of the present invention.

DETAILED DESCRIPTION OF THE PRESENT INVENTION

The present invention relates to a method to predict the rheological properties of a composition comprising a matrix and one or more fillers. In a preferred embodiment of the present invention, the method of predicting or determining the rheological properties of the composition is based on determining the contact angle of the filler based on one or more probe liquids. Preferably, the contact angle of the filler is based on at least three different probe liquids. The surface energy components of the filler are then determined based on the measured contact angles. The method further involves measuring the contact angle(s) of the matrix (in a fluid state) based on at least one solid. Various conditions, such as increasing temperature, may be needed in order to attain the fluid state for the matrix. Preferably, the contact angle is determined from the contact angle of the matrix based on three different solids. The surface energy components of the matrix are then determined based on the measured contact angle(s). Then, the work of adhesion and the work of cohesion are determined as well as the difference between the work of cohesion and work of adhesion. This data by itself can predict the yield point of the composition by correlating this data to a master curve or formula.

In the present invention, the composition comprises at least one filler in a matrix. For purposes of discussion, the term "filler" has been used but it is understood to mean particles such as carbon black particles and the like. Any filler can be used in the present application such as, but not limited to, carbon products such as carbon black, silica (fumed or precipitated), kaolin, talc, mica, glass beads and the like and combinations thereof.

With respect to the matrix of the composition, any matrix can be used. For example, the matrix may be a polymer or polymeric material, a solvent-resin system, or a solvent. When the matrix is a polymer or solvent-resin system, the polymer or resin can be a thermoplastic or thermoset polymer. Specific examples include, but are not limited to, polyurethane, polyacrylates, polymethacrylates, epoxies, and the like. Further, the polymer or resin can be a homopolymer, copolymer, terpolymer, and/or a polymer containing any number of different repeating units, and can be any type of polymer, such as a random polymer, alternating polymer, graft polymer, block polymer, star-like polymer, and/or comb-like polymer. The polymer or resin can also be one or more polyblends, an interpenetrating polymer network (IPN); simultaneous interpenetrating polymer network (SIN); or interpenetrating elastomeric network (IEN).

Specific examples of polymers or resins include, but are not limited to, linear-high polymers such as polyethylene, poly(vinylchloride), polyisobutylene, polystyrene, polycaprolactam (nylon), polyisoprene, and the like. Other general classes of polymers of the present invention are polyamides, polycarbonates, polyelectrolytes, polyesters, polyethers, (polyhydroxy)benzenes, polyimides, polymers containing sulfur (such as polysulfides, (polyphenylene) sulfide, and polysulfones), polyolefins, polymethylbenzenes, polystyrene and styrene copolymers (ABS included), acetal polymers, acrylic polymers, acrylonitrile polymers and copolymers, polyolefins containing halogen (such as polyvinyl chloride and polyvinylidene chloride), fluoropolymers, ionomeric polymers, polymers containing ketone group(s), liquid crystal polymers, polyamide-imides, polymers containing olefinic double bond(s) (such as polybutadiene, polydicyclopentadiene), polyolefin copolymers, polyphenylene oxides, poly(vinyl alcohols), polyurethanes, thermoplastic elastomers, and the like.

Generally, the polymers described in Volume 18 of the Encyclopedia of Chemical Technology, KIRK-OTHMER, (1982), page 328 to page 887, and Modern Plastics Encyclopedia '98, pages B-3 to B-210, and "Polymers: Structure and Properties," by C. A. Daniels, Technomic Publishing Co., Lancaster, Pa. (1989), all incorporated in their entirety herein by reference, can be used as the matrix for the compositions of the present invention. These polymers can be prepared in a number of ways and such ways are known to those skilled in the art. The above referenced KIRK-OTHMER section, Modem Plastics Encyclopedia, and C. A. Daniels' reference provide methods in which these polymers can be prepared.

With respect to determining the contact angle of the filler based on one or more probe liquids, the probe liquids can be any liquid. Preferably at least three probe liquids are used and these probe liquids are different from each other. Preferably the probe liquids are different from each other with respect to surface tension. For example, various properties of various probe liquids are identified in the example section which can be used in the present invention and include, but are not limited to, pentane, water, formamide, ethylene glycol, and the like.

The contact angle of the filler based on these probe liquids can be determined in any acceptable manner. For instance, and preferably, the filler is placed in a container such as a cell wherein the filler is packed into the cell. Preferably, the cell constant of the packed powder cell is determined by using a probe liquid such as pentane to determine the "cell constant." The wicking rate of the pentane is used to determine the "cell constant". A Kruss tensiometer can be used to determine this wicking rate. Based on this "cell constant," the contact angle of the pentane is assumed to be zero and the liquid is non-interacting with the filler surface. The cell constant is calculated according to equation (1):

$$C = \frac{m^2}{t} \cdot \frac{\eta}{\rho^2 \gamma} \quad (1)$$

wherein:
 m=Mass of liquid imbibed
 t=Time of wicking
 η=Viscosity of Pentane
 ρ=Density of pentane
 γ=Surface tension of Pentane
 C=Cell Constant Once the cell constant is determined, it can be used to determine the contact angles of the subsequent filler with the probe liquids. This data can then be used to plot a linear relationship that exists between the square of the mass and the time. A slope can be used to calculate the contact angle based on the pentane "cell constant" according to equation (2):

$$\cos(\theta) = \frac{m^2}{t} \cdot \frac{\eta}{\rho^2 \gamma C} \quad (2)$$

wherein:
 m=Mass
 t=Time
 η=Viscosity
 ρ=Density of liquid
 γ=Surface tension of liquid
 C=Cell Constant Once the contact angle of the filler or fillers is measured with a series of probe liquids, the contact angles determined from each liquid can be used to determine the surface energy components for each filler. The surface energy is calculated from the measured contact angles according to equation (3), where S (solid) refers to the filler and L (liquid) refers to the matrix:

$$\gamma_L(1+\cos\theta) = 2(\gamma_S^\delta \gamma_L^\delta)^{1/2} + 2(\gamma_S^+ \gamma_L^-)^{1/2} + 2(\gamma_S^- \gamma_L^+)^{1/2} \quad (3)$$

wherein:
 θ=Contact Angle
 $\gamma^+$=Lewis Acidity
 $\gamma^\delta$=Dispersive Component
 $\gamma_L$=Surface tension of the liquid
 $\gamma^-$=Lewis Basicity As can be seen above, the determination of the solid properties requires solving a system of three equations and three unknowns. The first step in the calculation involves a substitution of the contact angle for the filler for at least one probe liquid in the equation. This initial substitution determines the dispersive component of the filler. When the probe liquid used, for instance, has an acid and base component of zero, the calculation described above is quite possible. Thus, at least one probe liquid that has an acid and base component of zero is preferred, such as bromonaphthatene. With using such a probe liquid, the dispersive component of the solid is fixed and the other components of the surface free energy are calculated from the remaining contact angles and liquid property data substituted into equation (3).

As part of the method of the present invention, the contact angle of the fluid matrix on a solid is also obtained. Preferably, the contact angle of the matrix is based on at least three different solids, such as, but not limited to, polyethylene, polyvinylchloride, and polymethylmethacrylate. Preferably, at least one of these probe solids has an acid constant and a base constant of zero in order to easily determine the other variables in the contact angle equation, as discussed above for the filler.

Once the contact angles of the matrix, based on preferably at least three probe solids, is known, the surface energy components of the matrix can be determined. Once the surface energy components of the matrix are determined as well as the surface energy components of the filler, the work of adhesion of matrix to the filler and the work of cohesion of the filler can be determined. The difference between the work of cohesion and the work of adhesion can be determined, which can then be correlated to a particular rheological property, such as yield point, of the composition comprising the filler in the matrix.

In more detail, as part of the present invention, a rheological property of the composition is determined. Any rheological property of a matrix which is effected by the presence of a filler can be measured, such as, for example, the yield point (also known as Bingham yield), the viscosity at a defined shear rate, or the ratio of the change in viscosity to the change in shear rate. Other rheological properties will be known to one skilled in the art. By doing this actual measurement of the rheological property and comparing it to the difference in the work of cohesion and the work of adhesion, a rheological master curve and/or master formula can be created. Examples of a rheological master curve are shown below (FIGS. 2 and 3) and provide an indicator or prediction with respect to a filler-containing system and the rheological property, such as yield point, that will result. Thus, one knowing the difference in the work of cohesion and the work of adhesion for a particular composition comprising a filler in a matrix, one can immediately determine or predict the yield point that will be achieved by such a filler-matrix combination.

It is important to note that the rheological master curves apply to a particular filler loading, a particular morphology, and a particular temperature. For example, FIGS. 2 and 3 below are curves for a composition at a 10% filler loading. At other loadings or varying morphology (e.g., different DBPs), this rheological master curve and formula may shift to some extent based on the morphology of the filler and/or amount of loading in the matrix. Thus, various rheological master graphs or master formulas can be created depending on the loadings for various compositions and ultimately a third axis can be created to form a three-dimensional graph representing the effects of, for example, loading on the difference in the work of cohesion and the work of adhesion and yield point.

As shown in the rheological master curves below, once the difference in the work of adhesion and the work of cohesion are known for a particular composition, one can readily determine which filler to use in order to achieve the desirable yield point. Thus, in another embodiment, the present invention relates to a method of choosing a filler for a composition comprising a filler in a matrix. Knowing the desired yield point value, one could use the rheological master curve to determine the target difference between the work of cohesion of the desired filler and the work of adhesion of the matrix to the desired filler. Knowing or determining the surface energy components for the matrix will allow one to determine the surface energy components for the desired filler. This can be done, for example, by measuring the rheological properties of compositions containing various probe fillers, in which the surface energy properties of the probe fillers are known or measured (for example, using the methods described herein). Using the rheological master curve, the differences between the work of cohesion of each probe filler and the work of adhesion of the matrix to the probe filler can be obtained. Using the surface energy properties of the probe fillers, in combination with the correlated difference, one can calculate the surface energy components for the matrix. Now, having these values, and combining these with the desired rheolgical properties of the specific composition, one can determine what surface energy properties the target filler must have in order to achieve this property. Further, if a library of this data is kept, a particular filler can be immediately provided to obtain the desired rheological property. Alternatively, if such a filler is not available, a process could be developed for preparing the target filler having the desired surface energy components. Essentially, in one embodiment of the present application, the surface energies of the filler can be dialed in to ultimately form the desired yield point and other rheological properties of the polymer composition, which can be important in various applications of the composition in a variety of industries. For example, if one desires a composition having a high yield point, which is beneficial in such applications as adhesives and sealants, a filler would be chosen which gives a difference between the work of cohesion and the work of adhesion that is also relatively high. This is a direct result of the rheological master curves of the present invention and produced by the method of the present.

Accordingly, the rheological master curve and formula applies to all types of fillers and matrices and is quite useful once the difference in the work of cohesion and the work of adhesion are known. The ability to accurately predict the rheological properties (for example, yield point or stress) of a filler-containing composition as well as the ability to choose a filler to achieve a desired rheological property without the need for time consuming and expensive iterative evaluations thus provides one skilled in the art the ability to control the rheological properties of the composition. Thus, in another embodiment, the present invention relates to the ability to control and/or predict rheological properties based on the above-described procedure(s). Furthermore, the present application relates to compositions or systems comprising at least one filler in a matrix that are formed based on the methodology described above as well as the use of the rheological master curve and/or master formula.

The above-described embodiments of the present invention can be incorporated into computer programs and/or software to run the above-described methodologies. Also, in another embodiment, the above-described embodiments, can even be provided on the internet, for instance, through a website that permits end users to determine or find the appropriate filler for their matrix, or vice versa, in order to achieve certain desired rheological properties.

The present invention will be further clarified by the following examples, which are intended to be exemplary of the present invention.

EXAMPLES

Example 1

To show the determination of the master curve which correlates the difference between the work of cohesion and the work of adhesion to yield points, the following experiment was conducted. In addition, this experiment was also conducted in order to show the predictive value of the present invention as well as the ability of the present invention to determine yield points of various fillers.

The following describes a method for determining the wicking rates of various liquids into porous powder beds of carbon black particles. The wicking rates are subsequently used to calculate the contact angles of a probe liquid with a given carbon black surface. In turn, the surface free energy components of the carbon black are estimated from the contact angles by the van Oss approach.

The wicking rates of the liquids listed in Table 1 with various carbon black powders were measured using a Kruss K12 Tenisometer. The technique involved packing a FL-12 Kruss powder cell with the carbon black (or other filler). A single run involved the following:

TABLE 1

Properties of various probe liquids

| Liquid | Viscosity (mPas) | Surface Tension (mN/m) | Density (g/ml) | $\gamma d$ (mN/m) | $\gamma +$ (mN/m) | $\gamma -$ (mN/m) |
|---|---|---|---|---|---|---|
| Pentane | 0.24 | 15.5 | 0.629 | 15.5 | 0 | 0 |
| Water | 1 | 72.8 | 0.998 | 21.8 | 25.5 | 25.5 |
| Formamide | 3.81 | 58.2 | 1.133 | 39 | 2.28 | 39.6 |
| Ethylene Glycol | 21.81 | 48.3 | 1.109 | 29 | 1.92 | 47 |
| Bromonaphthalene | 5.11 | 44.6 | 1.483 | 44.4 | 0 | 0 |
| Tetrahydrofuran | 0.461 | 26.4 | 0.8844 | 27.4 | 0 | 15 |
| Diiodomethane | 2.76 | 50.8 | 3.325 | 50.8 | 0 | 0 |
| Methyl Sulfoxide (DMSO) | 2 | 44 | 1.101 | 36 | 0.5 | 32 |

An FL-12-PLP filter was placed into the bottom of the cell prior to the addition of 0.5–1.0 grams of carbon black powder. This prevented the powder from escaping from the bottom of the cell. The cap, which was equipped with a Teflon piston attached to a threaded shaft, was screwed to the top of the cell. The piston was then advanced by turning the plunger shaft until the bed was packed sufficiently. Typically, the number of shaft rotations were counted to consistently compress a given carbon black sample.

The packed powder cell was then placed on the K-12 tensiometer microbalance. The wicking rate of the pentane was used to determine the "cell constant". It was assumed that the contact angle of the pentane was zero and the liquid was non-interacting with the carbon black surface. The cell constant was calculated according to equation (1):

$$C = \frac{m^2}{t} \cdot \frac{\eta}{\rho^2 \gamma} \tag{1}$$

wherein:
  m=Mass of liquid imbibed
  t=Time of wicking
  η=Viscosity of Pentane
  ρ=Density of pentane
  γ=Surface tension of Pentane
  C=Cell Constant The cell constant was recorded and was used to determine the contact angles with subsequent probe liquids as listed in Table 1.

After each run, the cell was thoroughly cleaned. The carbon black and solvent was removed from the cell and discarded. The cell was then rinsed with acetone and was sonically cleaned in hexane. The cell was dried with a lint free cloth and further dried with compressed nitrogen.

In order to form the rheological master curve or formula, a correlation was determined between the surface energies of various fillers and the yield point that resulted from the composition containing the filler. The rheological master curve was created based on the data set forth in Table 2 below:

TABLE 2

Surface energy components of the selected carbon black samples

| Sample | $\gamma^d$ (mN/m) | $\gamma^+$ (mN/m) | $\gamma^-$ (mN/m) |
|---|---|---|---|
| Carbon Black A | 21.1 | 5.20 | 0.45 |
| Carbon Black B | 19.00 | 12.4 | 0 |
| Carbon Black C | 34 | 5.9 | 0 |

Determination of Yield Points

Figure 1:
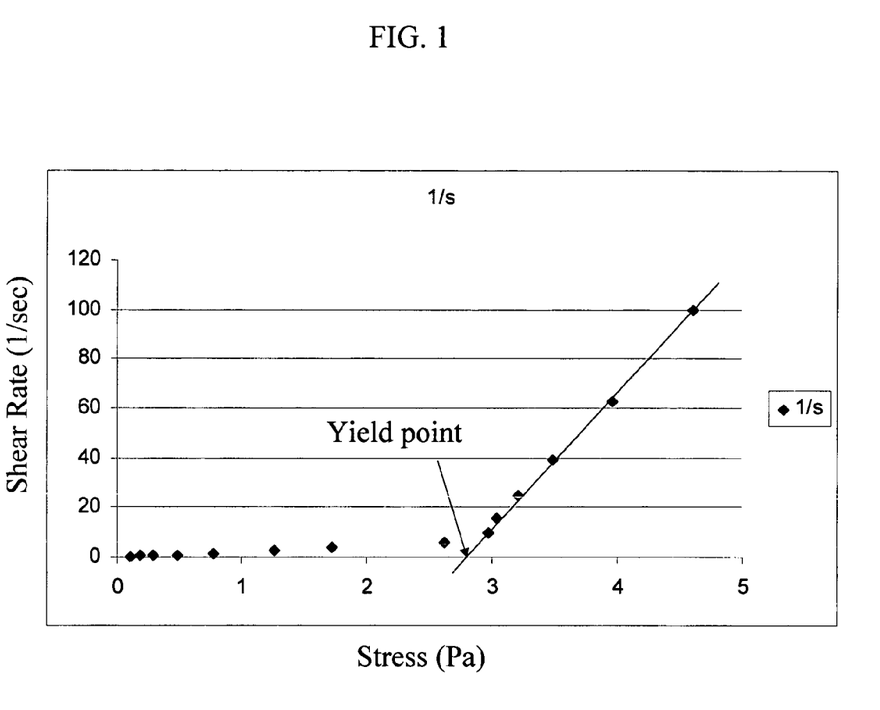
FIG. 1 is a graph plotting shear rate versus shear stress for determining yield.

Yield points were determined using the following procedure. Ten (10) wt percent black was mixed with in each of the follow: Ethylene glycol, dimethyl sulfoxide, mineral oil, polydimethyl siloxane. Each mixture was placed in a "midgit mill" containing small shot. The mill was placed on a paint shaker and mixed for 30 minutes. The samples were filtered using a paint strainer to remove the shot. The samples were then tested on a Carri-Med rheometer for yield evaluation. FIG. 1 gives typical results of the measured stress—strain plot obtained from the rheometer. The yield points determined in this way were plotted against the (Work of cohesion-Work of adhesion) determined as shown in more detail below.

Analysis of Data

A Kruss Tensiometer was attached to a computer that records the raw data file. The data was recorded as the mass of imbibed liquid as a function of time. It was determined that a linear relationship existed between the mass squared and time. The data was analyzed over the most linear region of the curve. The slope was used to calculate the contact angle based on the pentane "cell constant" according to equation (2):

$$\cos(\theta) = \frac{m^2}{t} \cdot \frac{\eta}{\rho^2 \gamma C} \tag{2}$$

wherein:
  m=Mass
  t=Time
  η=Viscosity
  ρ=Density of liquid
  γ=Surface tension of liquid
  C=Cell Constant Calculation of Surface Energy from Contact Angles Carbon black samples were measured with a series of probe liquids as described above. The contact angles determined from each liquid were then used to calculate the surface energy components for each carbon black. The surface energy was calculated from the measured contact angles according to the van Oss/Good approach equation (3). In order to solve for the three components (Dispersive, Acid, and Base) at least three probe liquids were used.

$$\gamma_L(1+\cos\theta) = 2(\gamma_S^d \gamma_L^d)^{1/2} + 2(\gamma_S^+ \gamma_L^-)^{1/2} + 2(\gamma_L^+ \gamma_S^-)^{1/2} \tag{3}$$

wherein:
  θ=Contact Angle
  $\gamma^d$=Dispersive Component
  $\gamma_L$=Surface tension of the liquid
  $\gamma^+$=Lewis Acidity
  $\gamma^-$=Lewis Basicity The determination of the solid properties involved solving a system of three equations for three unknowns. The first step in the calculation involved the substitution of the contact angle for the carbon black/bromonaphthalene experiment (and the properties of bromonapthalene) into the van Oss/Good equation. This initial substitution determined the dispersive component of the carbon black. This calculation was possible because the Acid and Base components of Bromonaphthalene are both zero. The now known dispersive component of the solid was fixed. The other components of the surface free energy were then calculated from remaining contact angle and liquid property data substituted into equation (3).

The second part of the experiment was to characterize the matrix. Several approaches could be taken, which are described in more detail below.

Method A

The properties of the fluid matrix were determined from the contact angle of the fluid on three different solids, e.g. polyethylene, polyvinylchloride, and polymethylmethacrylate. From these three contact angles, the characteristic surface tension components for the matrix were determined by the method of van Oss and Good as follows. (van Oss, C. J. "Interfacial forces in aqueous media"; Marcel Dekker: New York; 1994, incorporated in its entirety by reference herein).

The three contact angles can be measured by any appropriate technique, such as Morrison, I. D.; Ross, S. "Colloidal Dispersions"; John Wiley & Sons: New York; 2002, pp. 208–214, incorporated in its entirety by reference herein. The surface tension of the fluid matrix can be measured by any appropriate technique such as Morrison, pp. 200–208, incorporated by reference herein.

The relation between the measured contact angle, θ, and measured surface tension of the fluid matrix, $\gamma_L$, on a given solid is given by equation (4) (van Oss, C. J. p. 22, equation III-13):

$$(1+\cos\theta)\gamma_L = 2(\sqrt{\gamma_S^d \gamma_L^d} + \sqrt{\gamma_S^+ \gamma_L^-} + \sqrt{\gamma_S^- \gamma_L^+}) \quad (4)$$

The known surface energy components for the three solids is given in Table 3 below:

TABLE 3

Surface tension components for standard polymers, at 20° C. in mN/m

| Polymer | Dispersion constant $\gamma_S^d$ | Acid constant $\gamma_S^+$ | Base constant $\gamma_S^-$ |
|---|---|---|---|
| Polyethylene | 33.0 | 0 | 0 |
| Polymethylmethacrylate (PMMA) | 40.0 | 0 | 14.6 |
| Polyvinylchloride | 43.0 | 0.04 | 3.5 |

The three unknowns are the three components of the surface energy of the matrix. By measuring three contact angles, all three unknowns can be determined and the fluid matrix characterized.

Method B

Alternatively, the properties of the fluid matrix can be estimated by choosing a polymer to which it best corresponds. Table 4 shows various polymers and their surface tension components (from van Oss, p. 16.). The important correspondence is its Lewis acid or Lewis base strength. (See Jensen, W. B. "The Lewis acid-base concepts"; John Wiley & Sons: New York; 1980 for an explanation of the key ideas, incorporated in its entirety by reference herein.) Further approximations can be made by using an appropriate average of similar polymers.

TABLE 4

Surface tension components of various synthetic polymers, at 20° C. in mN/m

| Polymer | Dispersive | Acid | Base |
|---|---|---|---|
| Teflon FEP | 17.0 | 0 | 0 |
| Nylon 6.6 | 36.4 | 0.02 | 21.6 |
| Polyisobutylene | 25 | 0 | 0 |
| Polypropylene | 25.7 | 0 | 0 |
| Corna-treated polypropylene | 33.0 | 0 | 11.1 |
| Polyethylene | 33.0 | 0 | 0 |
| Polymethylmethacrylate (PMMA) | 40.0 | 0 | 14.6 |
| Polystyrene | 42 | 0 | 1.1 |
| Polyvinylpyrrolidone | 43.4 | 0 | 29.7 |
| Polyvinylchloride | 43.0 | 0.04 | 3.5 |
| Polyethyleneoxide | 43 | 0 | 64 |

Method C

Also, the properties of the fluid matrix can be estimated by choosing a liquid to which the fluid matrix best corresponds. The correspondence depends on the chemical nature, not the molecular weight of the matrix. The important chemical nature is taken to be the Lewis acid or Lewis base strength of the matrix. (See Jensen, W. B. "The Lewis acid-base concepts"; John Wiley & Sons: New York; 1980 for an explanation of the key ideas.) Values of the dispersion, acid, and base components of various common solvents are given in van Oss, pp. 172–173, incorporated in its entirety by reference herein.

Method D

Alternative methods to characterize the fluid matrix can also be used. Some of these are referred to in a review of the subject, Clint, J. H. "Adhesion and components of solid surface energies." Current Opinion in Colloid & Interface Science, 2001, 6, 28–33 and in the book, Berg, J. C., Ed. "Wettability" Marcel Dekker: New York; 1993, incorporated in its entirety by reference herein.

Method E

Another way to characterize the fluid matrix is to measure its wicking time on powders of known composition. The wicking of a liquid up a bed of packed powder is a method to determine the contact angle of a liquid on a solid (the Washburn method). The relation between the rate of wicking, $L/t^2$, and the contact angle of a liquid of known surface tension, $\sigma_{matrix}$, and viscosity, $\eta$ is given by equation (5):

$$\frac{L^2}{t} = \frac{r}{2\eta}\sigma_{matrix}\cos\theta \quad (5)$$

wherein r is found the usual way by measuring the wicking rate of a hydrocarbon liquid (equation (6)):

$$r = \frac{2\eta_{hc}}{\sigma_{hc}}\frac{L^2}{t_{hc}} \quad (6)$$

Figure 2:
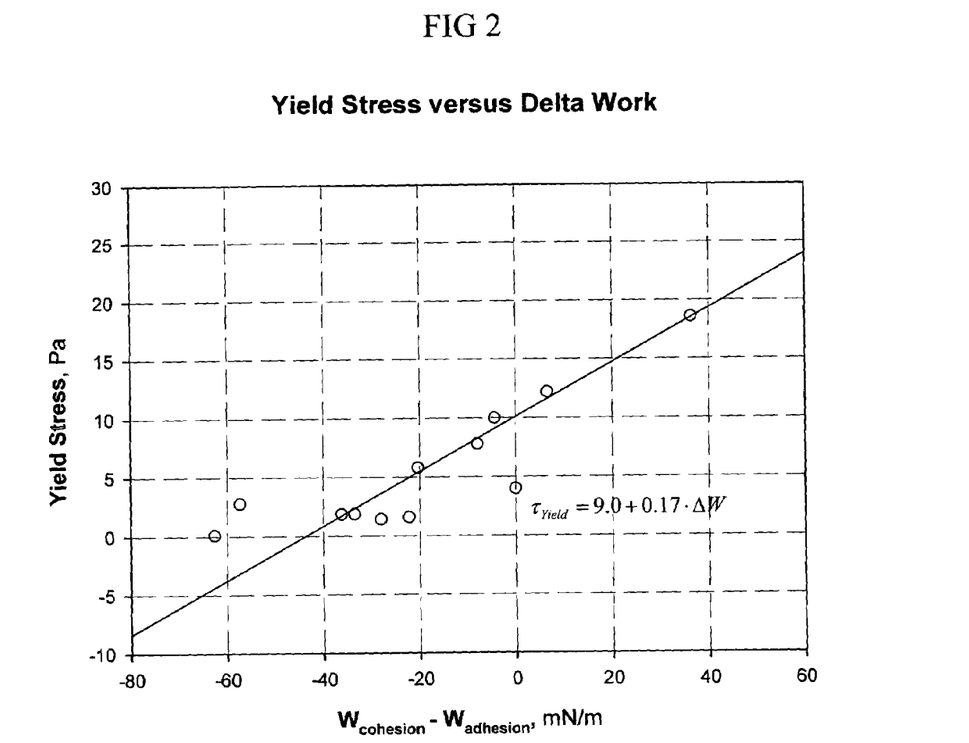
FIG. 2 is a master curve showing the general correlation of work of cohesion minus work of adhesion and yield point.

FIG. 2 shows the relation between the thermodynamic quantity, $W^{coh}-W^{adh}$ and the yield point. The work of cohesion is just twice the surface tension of the solid (equation (7)):

$$W^{coh}=2\sigma_{solid} \quad (7)$$

The work of adhesion is given by equation (8):

$$W^{adh} = \sigma_{liquid}(1+\cos\theta) = \frac{2\eta}{r}\frac{L^2}{t} + \sigma_{liquid} \quad (8)$$

Therefore, as shown in equation (9):

$$W^{adh} - W^{coh} = \frac{2\eta}{r}\frac{L^2}{t} + \sigma_{liquid} - 2\sigma_{solid} \quad (9)$$

Considering this equation between wicking rates and the thermodynamics of particle structure in liquids and the relation between the thermodynamic function and yield points shown in the graph shows that wicking rates and yield points are related.

Calculation of Work of Adhesion and Work of Cohesion.

The work of adhesion between a solvent or a polymer of interest and the carbon black is calculated using the equation (10).

$$W^{adh}=2(\gamma_S^d \gamma_L^d)^{1/2}+2(\gamma_S^+ \gamma_L^-)^{1/2}+2(\gamma_L^+ \gamma_S^-)^{1/2} \quad (10)$$

The surface free energy components are known for the given carbon back and polymer. Thus the free energy of interaction can be quantitatively determined. Likewise the work of cohesion is calculated by using equation (11) and equation (12).

$$W_S^{coh} = 2\gamma_S^d + 2(\gamma_S^+ \gamma_S^-)^{1/2} \quad (11)$$

$$W_L^{coh} = 2\gamma_L \quad (12)$$

Figure 3:
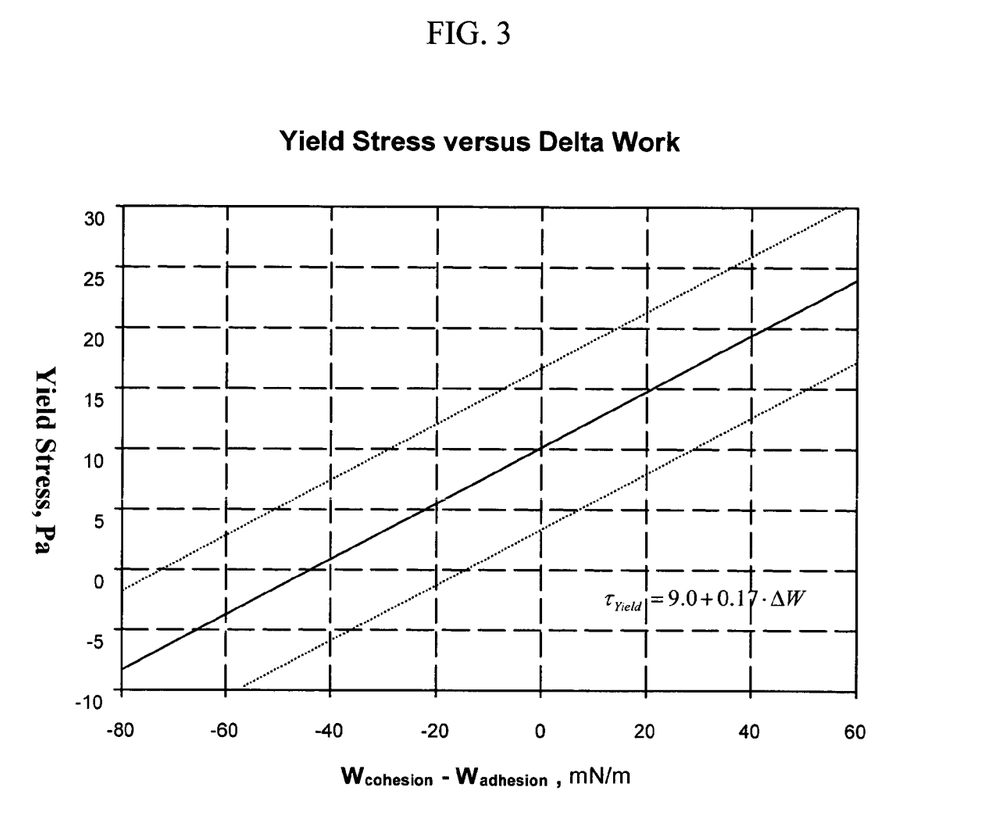
FIG. 3 is a master curve illustrating ranges of work of cohesion minus work of adhesion for a particular yield point.

FIG. 3 is a master curve illustrating ranges, within the upper and lower lines, of work of cohesion minus work of adhesion for a particular yield point.

Example 2

To show the determination of the rheological master curve which correlates the difference between the work of cohesion and work of adhesion and yield points in a single liquid at higher filler weight content than Example 1, the following experiment was conducted. In addition, the experiment illustrates the predictive value of the present invention as well as the ability of the present invention to determine yield points of various fillers using a single liquid and high weight percent filler. The method of determining the wicking rates of various liquids into porous powder beds of carbon black particles was the same as that described in Example 1.

In order to form the rheological master curve or formula, a correlation was determined between the surface energies of various fillers and the yield point that resulted from the composition containing the filler. The rheological master curve was created based on the data set forth in Table 5 below:

TABLE 5

Surface Energy Components of Selected Carbon Black Samples

| Sample | $\gamma^d$ (mN/m) | $\gamma^+$ (mN/m) | $\gamma^-$ (mN/m) |
|---|---|---|---|
| Carbon Black E | 14.8 | 35.2 | 8.8 |
| Carbon Black F | 14.3 | 39.5 | 9.3 |
| Carbon Black G | 14.2 | 32.7 | 13.5 |
| Carbon Black H | 19.8 | 38.8 | 7.9 |
| Carbon Black I | 39.3 | 3.13 | 14.5 |
| Carbon Black J | 17.6 | 28.5 | 14.2 |

Determination of Yield Points

Yield points were determined using the following procedure. Fifteen (15) wt percent black was mixed with Ethylene Glycol. The mixture was placed in a "midgit mill' containing small shot. The mill was placed on a paint shaker and mixed upto 30 minutes. The samples were separated from the shot and subsequently tested for yield point on a Carri-Med rheometer in a similar manner described in Example 1.

Figure 4:
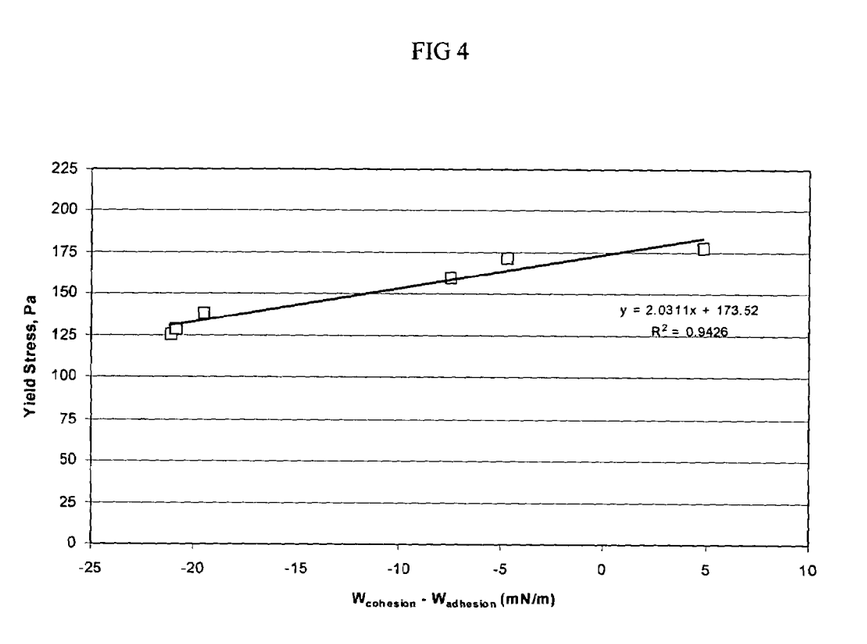
FIG. 4 is a master curve relating the difference between the work of cohesion work of adhesion for a single fluid.

The analysis of the data was performed similar to that described in Example 1. Results are shown in FIG. 4 below, which is a rheological master curve relating yield point to the difference between the work of cohesion and the work of adhesion for a single fluid.

As can be seen, the present invention has the ability to predict quite effectively the yield points of a polymer-filler system. Furthermore, with the creation of the master curve, once one knows the work of adhesion and the work of cohesion, one can immediately predict the yield point of a filler in a polymer system.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for determining a rheological master curve for a composition comprising a filler in a matrix, wherein the method comprises the steps of:
    a) determining the work of adhesion of the matrix to the filler;
    b) determining the work of cohesion of the filler;
    c) determining the difference between the work of cohesion and the work of adhesion;
    d) measuring a rheological property of the composition; and
    e) correlating the rheological property to the difference between the work of cohesion and the work of adhesion.

2. The method of claim 1, wherein the steps of determining the work of adhesion and of determining the work of cohesion comprises the steps of:
    a) determining the contact angles of the filler based on one or more probe fluids;
    b) determining the surface energy components for the filler based on the measured contact angles of the filler;
    c) determining the contact angles of the matrix based on one or more probe solids; and
    d) determining the surface energy components of the matrix based on the measure contact angles of the matrix.

3. The method of claim 1, wherein the rheological property is yield point, viscosity at a defined shear rate, or the ratio of the change in viscosity to change in shear rate.

4. The method of claim 3, wherein the rheological property is yield point.

5. A rheological master curve for a composition comprising a filler in a matrix, obtained by the method of claim 1, wherein the master curve correlates i) the difference between the work of cohesion of the filler and the work of adhesion of the matrix to the filler; and ii) a rheological property of the composition.

6. A rheological master curve for a composition comprising a filler in a matrix, wherein the master curve correlates i) the difference between the work of cohesion of the filler and the work of adhesion of the matrix to the filler; and ii) a rheological property of the composition, wherein the rheological property is yield point, viscosity at a defined shear rate, or the ratio of the change in viscosity to change in shear rate.

7. The rheological master curve of claim 6, wherein the rheological property is yield point.

8. A method of predicting a value for a rheological property of a composition comprising a filler in a matrix, wherein the method comprises the steps of:
    a) determining the work of adhesion of the matrix to the filler;
    b) determining the work of cohesion of the filler;
    c) determining the difference between the work of cohesion and the work of adhesion; and
    d) correlating the difference between the work of cohesion and the work of adhesion to the value for the rheological property using the rheological master curve of claim 5.

9. The method of claim 8, wherein the rheological property is yield point, viscosity at a defined shear rate, or the ratio of the change in viscosity to change in shear rate.

10. The method of claim 9, wherein the rheological property is yield point.

11. A method of choosing a target filler to achieve a desired value of a rheological property of a composition comprising the target filler in a matrix, wherein the method comprises the steps of:

a) determining the surface energy components for several probe fillers;
b) measuring the rheological property of a composition comprising one probe filler and the matrix;
c) correlating the rheological property of the composition comprising the probe filter and the matrix to a difference between the work of cohesion of the probe filler and the work of adhesion of the matrix to the probe filler using the rheological master curve of claim 5;
d) repeating steps b) and c) for each probe filler;
e) calculating the surface energy components of the matrix using the correlated difference of step c) and the surface energy components of the probe fillers of step a);
f) correlating the desired value of the rheological property of the composition comprising the target filler in the matrix to a difference between the work of cohesion of the target filler and the work of adhesion of the matrix to the target filler using the rheological master curve;
g) choosing the target filler having the surface energy components which, when used to calculate the work of cohesion of the target filler and the work of adhesion of the matrix to the target filler, gives a difference which is similar to the correlated difference of step f).

* * * * *